United States Patent [19]

Mathys

[11] Patent Number: 5,403,136
[45] Date of Patent: Apr. 4, 1995

[54] THREADED FASTENER ESPECIALLY FOR ORTHOPAEDIC PURPOSES

[75] Inventor: Robert Mathys, Bettlach, Switzerland

[73] Assignee: Synthes (U.S.A.), Paoli, Pa.

[21] Appl. No.: 975,577

[22] PCT Filed: Jun. 24, 1992

[86] PCT No.: PCT/CH92/00122
§ 371 Date: Feb. 9, 1993
§ 102(e) Date: Feb. 9, 1993

[87] PCT Pub. No.: WO93/00518
PCT Pub. Date: Jan. 7, 1993

[30] Foreign Application Priority Data
Jun. 25, 1991 [CH] Switzerland ............... 1875/91

[51] Int. Cl.⁶ ............... F16B 35/04; F16B 39/30; A61F 5/04
[52] U.S. Cl. ............... 411/310; 411/263; 411/413; 411/426; 606/73
[58] Field of Search ............... 411/263, 306-310, 411/415, 426, 413; 606/65, 73

[56] References Cited

U.S. PATENT DOCUMENTS

| 146,023 | 12/1873 | Russell | 411/415 |
|---|---|---|---|
| 2,419,555 | 4/1947 | Fator | 411/413 X |
| 3,233,500 | 2/1966 | De Vellier . | |
| 3,454,070 | 7/1969 | Phipard, Jr. | 411/307 X |
| 3,664,540 | 5/1972 | Witkin . | |
| 4,175,555 | 11/1979 | Herbert | 411/415 X |
| 4,842,464 | 6/1989 | Green . | |
| 4,892,429 | 1/1990 | Giannuzzi | 411/426 |
| 5,120,171 | 6/1992 | Lasner | 411/308 |
| 5,147,363 | 9/1992 | Harle | 606/73 |

FOREIGN PATENT DOCUMENTS

| 282789 | 9/1988 | European Pat. Off. | 606/73 |
|---|---|---|---|
| 424734 | 5/1991 | European Pat. Off. . | |
| 2609757 | 7/1988 | France . | |
| 2211416 | 5/1989 | United Kingdom . | |

Primary Examiner—Neill R. Wilson
Attorney, Agent, or Firm—Davis Hoxie Faithfull & Hapgood

[57] ABSTRACT

The fastener, which is especially adapted for bones, consists of a shaft (2) bearing a thread (1) with variable pitch, a front end (3) and a rear end (4).

The thread (1) is present over the entire area of the shaft (2), and in the area of the rear end (4) is characterized by a smaller pitch than in the area of the front end (3).

Thanks to the diminishing pitch of the thread (1) in the proximal direction, a locally differentiated intraosseous pressure generation takes place. In accord with the well-known Wolff's Law, this leads to a controlled bone growth along the loading axis and thus an improvement in the stability of the implanted fastener.

5 Claims, 6 Drawing Sheets

THREADED FASTENER ESPECIALLY FOR ORTHOPAEDIC PURPOSES

FIELD OF THE INVENTION

This invention relates to a fastener, specifically a threaded fastener especially for orthopaedic purposes.

BACKGROUND OF THE INVENTION

A generic fastener, in the form of a bolt, is already known from DE-C2 2,807,364. This previously known fastener, conceived as a bone screw, consists of a threadless middle section, to which are attached, both in the upper, proximal part and the lower, distal part, threads with differing diameters, and pitches which differ from each other but are nonetheless constant in each part. Therefore prior to inserting the bone screw, it is necessary to drill holes of differing diameters with corresponding threads having different diameters but a constant pitch, in each of the bone fragments that are to be joined together. If a thread with a smaller pitch is employed for the proximal part of the shaft, then in screwing in this previously known bone screw, the effect is to bring the two bone fragments closer together and to correspondingly compress the fracture surfaces.

A disadvantage of this previously known fastener, designed according to the principle of two threads with differing pitch, is that it has a threadless midsection, and that the differing distal and proximal threads both have constant pitches. This allows merely a compression between two loose bone fragments, but does not permit a local intraosseous pressure generation which would be desirable for a whole range of applications.

With the previously known fastener, as well as with the other bone screws, what is lacking is a differentially acting force in the proximal area, so that in the proximal area again and again we encounter a zone of small bone thickness, which results in reduced stability of the implant.

SUMMARY OF THE INVENTION

In this regard the invention will afford a remedy. At the basis of the invention is the task of creating a threaded fastener which can be screwed into a material that is at least slightly elastically compressible, such as bone material or wood. The fastener can either make its own incision or be screwed into a pre-cut thread with a constant pitch. Thus, it can create, in bone material for example, a locally differentiated intraosseous pressure, which can be made to adapt to the biological requirements concerning force application and the local loading of the material. The invention solves the problem with a fastener that demonstrates the features of claim 1.

The advantages obtained from the invention are in essence as follows. Thanks to an invention-specific pitch (which preferably diminishes constantly) of the thread in the proximal direction, a locally differentiated intraosseous pressure generation takes place in bones. In accord with the well-known Wolff's Law, this leads to controlled bone growth along the loading axes.

The good bone thickness achieved thereby in this delicate area results in a stable integration of the implant.

BRIEF DESCRIPTION OF THE DRAWINGS

An application example for the invention, which elucidates its functional principle at the same time, is depicted in the drawings, in which.

DETAILED DESCRIPTION OF THE PREFERRED EMBODIMENTS

Figure 1:
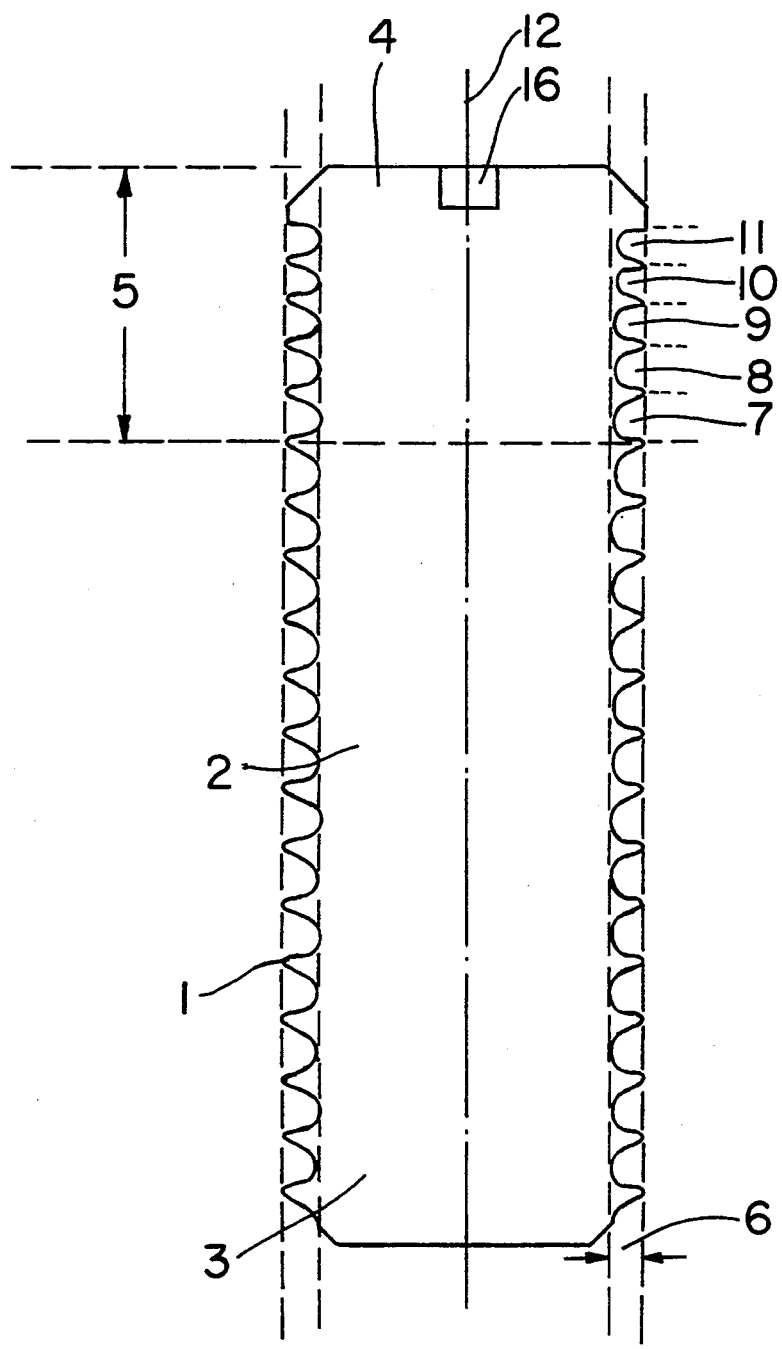
FIG. 1 depicts a cross section through the fastener of the invention.

In essence the invention-specific fastener depicted in FIG. 1 consists of a circular cylindrical shaft 2 possessing a thread 1, a front end 3, a rear end 4 and a rotational axis 12. The rear end of the shaft 2 is provided with a slot or hexagonal recess 16, into which an appropriate tool (screwdriver, hex wrench) can be inserted, to permit screwing the fastener in or removing it. The thread 1 in this preferred design configuration is self-cutting, and it extends over the entire area of the shaft 2. While the thread 1 in the front end area 3 has a constant pitch of, for example, one millimeter per thread convolution, the pitch in section 5 varies from convolution to convolution. Convolution 7 still shows a pitch of 0.95 mm; convolution 8, of 0.9 mm; convolution 9, of 0.85 mm; convolution 10, of 0.80 mm, and convolution 11, of 0.75 mm. By this means a differential intraosseous pressure can be generated, with the elastic material into which the fastener is being screwed being compressed into the diminishing convolution.

Figure 2:
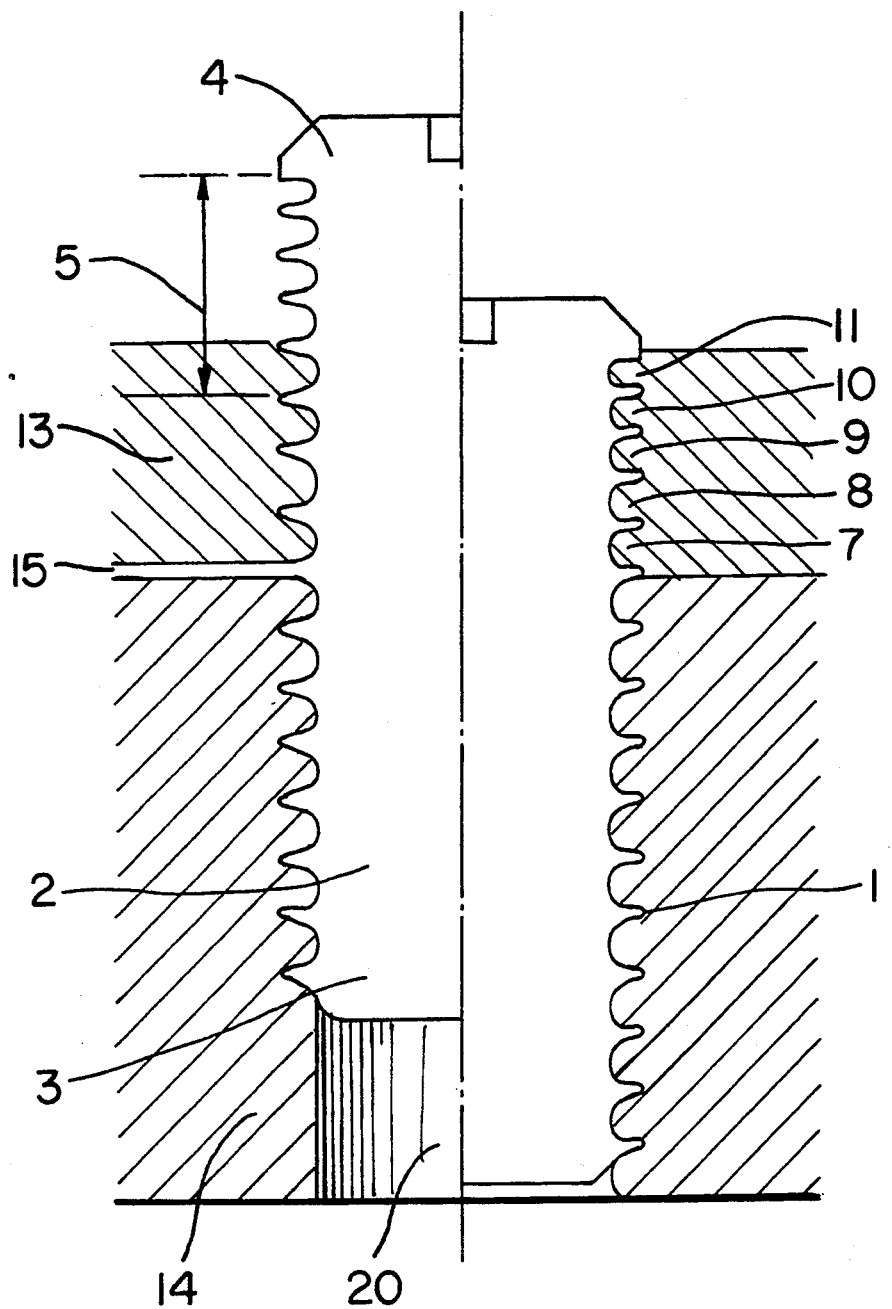
FIG. 2 depicts a cross section through the fastener according to FIG. 1. The left half of the picture shows the initial phase of screwing in, and the right half of the picture shows the concluding phase after screwing into the bone is complete.

In FIG. 2 one can see an application of the invention-specific fastener, in which two elements are pressed against each other. It is especially suited for securing a bone transplant in bone surgery. However, it may be utilized as a connecting device for other materials, such as soft wood, for example.

In the left half of the picture is depicted the situation that arises following the screwing in of the front end 3 (possessing constant thread pitch) of the shaft 2 through the predrilled core removal hole 20 in a jaw 14, and through the transplant layer 13. The 0.20 mm-wide unwanted crack between transplant layer 13 and jawbone 14 is retained until this screwing-in phase. As soon as section 5 of the rear end, equipped with diminishing pitch of thread 1, is screwed in, the result is a different amount of fastener distance covered, owing to the comparatively smaller thread pitch in the area of the jawbone 14. After screwing in thread convolutions 7-10 (with a total difference of 0.20 mm), this results in a complete closure of the 0.20-mm-wide crack 15. As depicted in the right half of the picture, it also results ultimately in an intraosseous compression, which—thanks to the pitch that diminishes from convolution to convolution of the thread in area 5—gradually reduces toward the rear end 4. This is biologically desirable.

Figure 3:
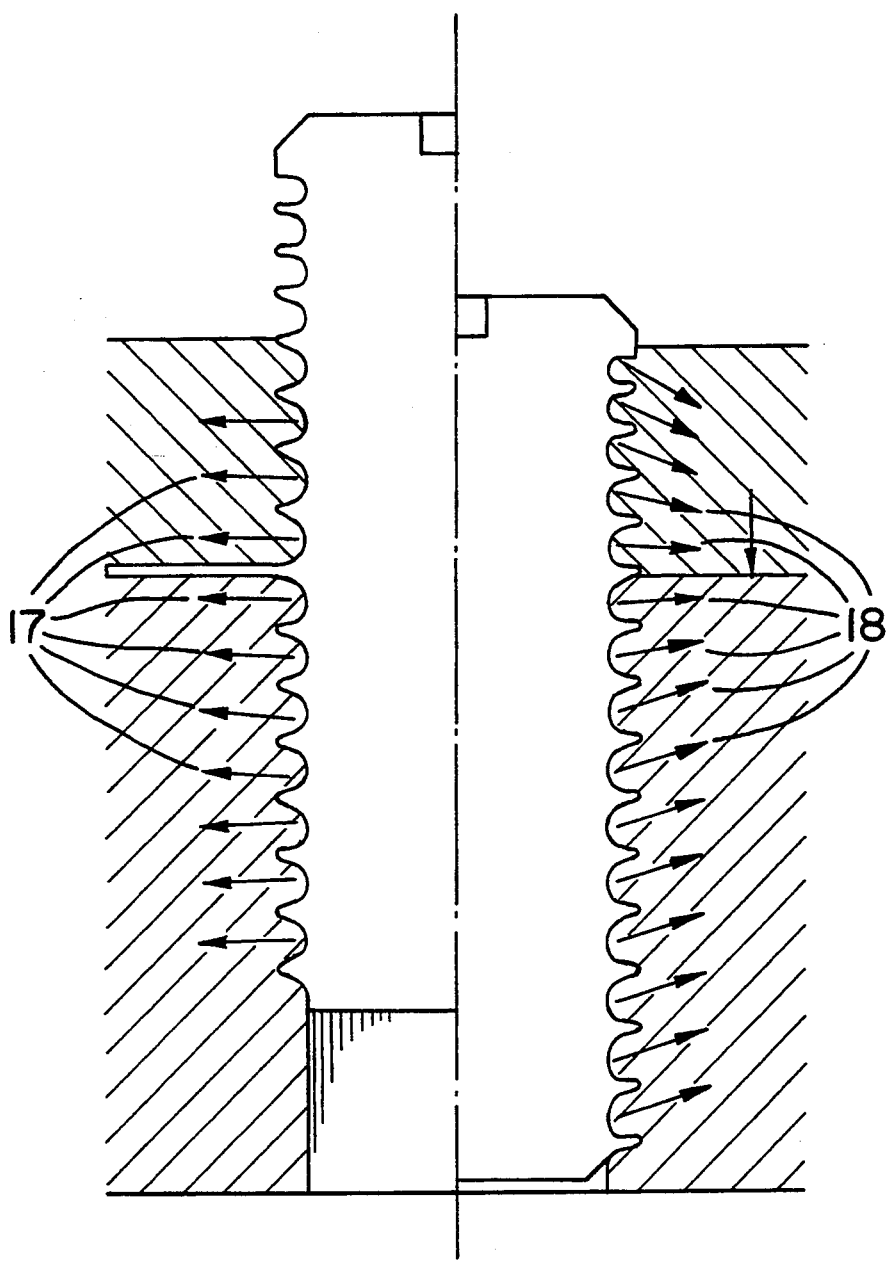
FIG. 3 depicts a partial cross section of the fastener of the invention with the forces present as in FIG. 2.

The forces that arise at the top of the individual thread convolutions in making the transition from the intermediate screwing-in phase (as depicted on the left half of the picture) to the concluding phase (in the right half of the picture), are indicated in FIG. 3 by the arrows 17 (indicating the intermediate screw-in phase without compression) and the arrows 18 (concluding phase with compression).

Figure 4:
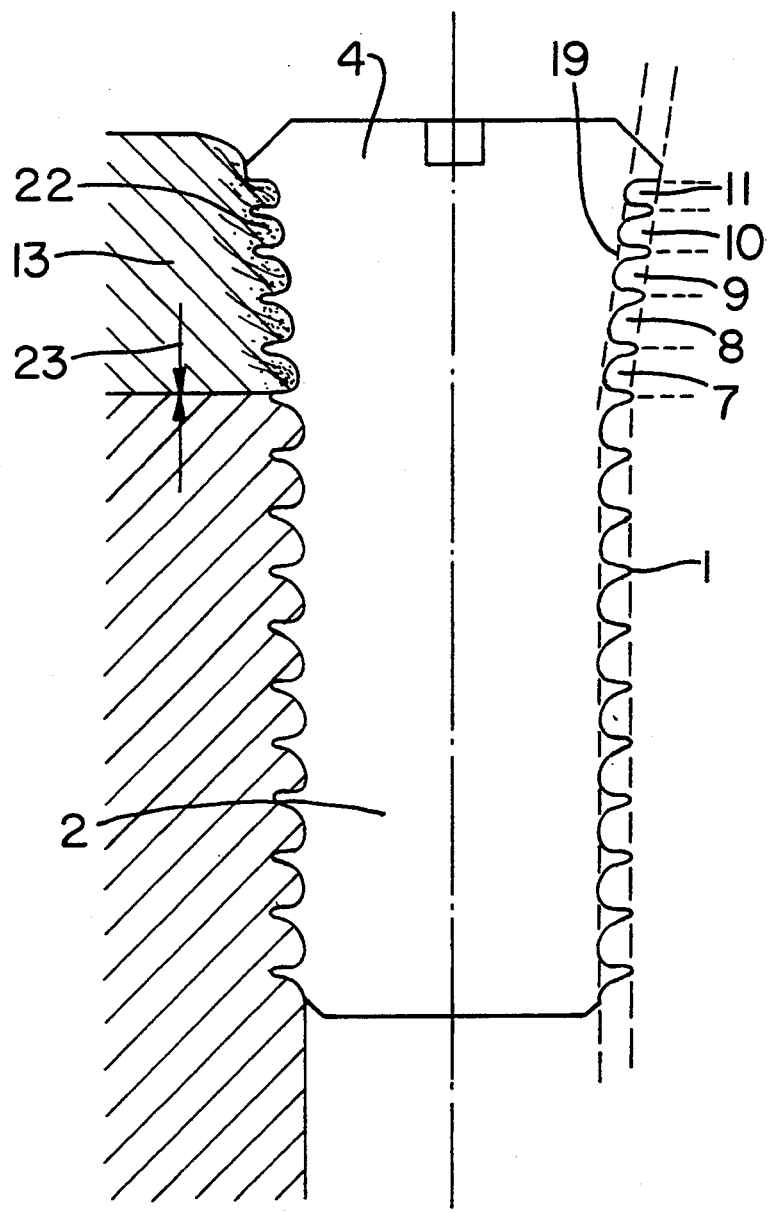
FIG. 4 depicts a cross section through a fastener of the invention with a conical head section.

With a preferred design configuration of the invention-specific fastener, as shown in FIG. 4, the rear end 4 of shaft 2 has a conical form, in which the cone 19 broadens out toward the rear end 4. In the circular-cylinder area of the shaft 2, the thread 1 possesses a constant pitch of 1.0 mm, while in the extended area of the cone 19 the pitch of thread 1 diminishes continuously toward the rear end 4.

In the left half of the picture is a depiction of how the volume of material 22 of bone transplant 13, as encompassed by thread 1, is pressed into the volumetrically smaller thread convolutions 7–11. This takes place when thread convolutions 7–11 of the conical section, having diminishing pitch, are screwed in. This results in a locally differentiated pressure which is simultaneously transformed into an axially operating force (indicated by arrow 23).

This partially conical design configuration of the invention-specific fastener results in additional securing effectiveness in comparison with the circular cylinder configuration as per FIGS. 1–3.

Figure 5:
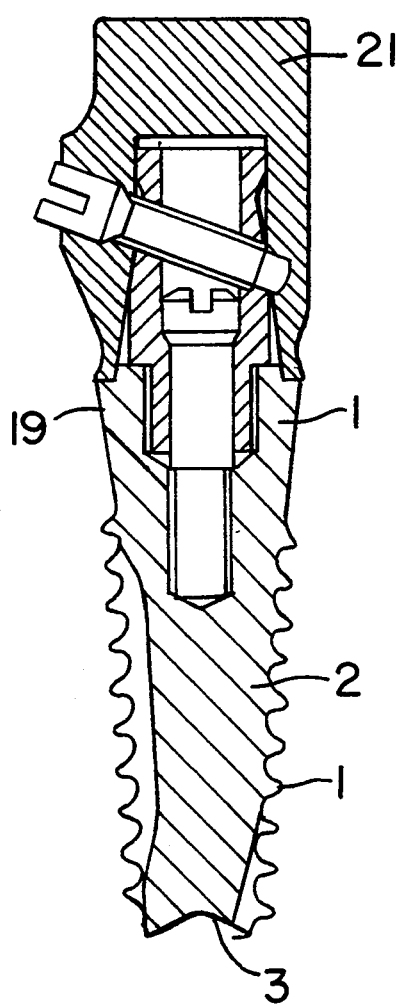
FIG. 5 depicts a cross section of the fastener of the invention in the form of a dental implant with a cone, in which the thread shows a differentiated, diminishing pitch toward the cone.

With an additional application configuration according to FIG. 5, the invention-specific fastener is depicted as a dental implant. On the rear end 4, the superstructural elements 21 common to dental implants are attached. In the remaining portion, the shaft 2 with thread 1 is configured conically toward the front end 3. The thread 1 extends from the front end 3 to the rear end 4 formed as a cone 19. The cone 19 itself is unthreaded, as is customary for supergingival implants.

Figure 6:
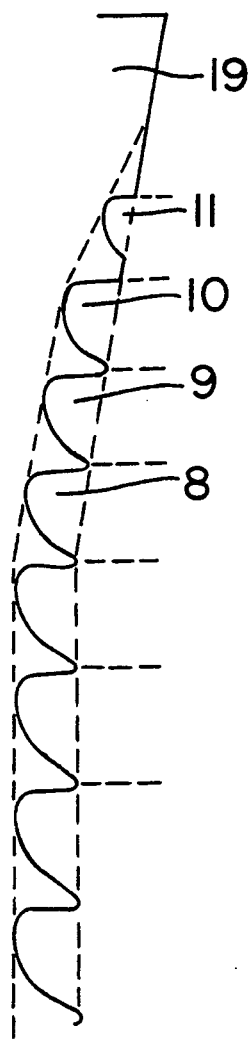
FIG. 6 depicts a partial cross section through the thread of the fastener in accord with FIG. 4.

In a configuration for subgingival dental implants depicted in part in FIG. 6, the cone 19 is equipped in part with thread convolutions 8–11, whose pitch diminishes in the proximal direction.

Figure 7:
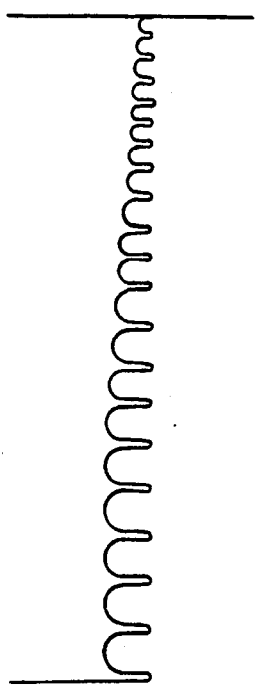
FIG. 7 is a schematic view illustrating the thread of a fastener according to the invention in which the depth of the thread is reduced toward the rear end.

FIG. 7 illustrates how the depth of the thread may diminish with decreasing pitch toward the rear end of the fastener.

The invention-specific fastener can be fabricated from any metal suitable for screws. However, in using it as a dental implant, preferably pure titanium will be used.

What is claimed is:

1. A fastener comprising a cylindrical shaft having a front end and a rear end and a thread extending over the entire area of the shaft, said thread at said front end being of substantially constant pitch and rearward of said front end diminishing in pitch and in depth toward said rear end.

2. The fastener according to claim 1 wherein the pitch of the thread diminishes in at least one section by 0.04 to 0.06 mm per thread convolution.

3. The fastener according to claim 1 wherein the thread, at least in one section has a continuously diminished pitch from the front section to the rear end.

4. The fastener according to claim 1 wherein the thread is self-tapping.

5. A dental implant comprising the fastener of claim 1.

* * * * *